US009839343B2

(12) United States Patent
Oginski et al.

(10) Patent No.: US 9,839,343 B2
(45) Date of Patent: Dec. 12, 2017

(54) ROTATIONAL DEVICE AND METHOD FOR ROTATING AN ENDOSCOPE

(71) Applicant: Karl Storz SE & Co. KG, Tuttlingen (DE)

(72) Inventors: Stefan Oginski, Fulda (DE); Daniel Brueggemann, Lippstadt (DE); Robert Dreyer genannt Daweke, Berlin (DE); Christian Ramsch, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 10 days.

(21) Appl. No.: 14/518,644

(22) Filed: Oct. 20, 2014

(65) Prior Publication Data
US 2015/0105620 A1 Apr. 16, 2015

Related U.S. Application Data

(63) Continuation of application No. PCT/DE2013/200010, filed on Apr. 18, 2013.

(30) Foreign Application Priority Data

Apr. 18, 2012 (DE) .................. 10 2012 206 412

(51) Int. Cl.
*A61B 1/00* (2006.01)
*A61B 1/04* (2006.01)
(Continued)

(52) U.S. Cl.
CPC ........ *A61B 1/00121* (2013.01); *A61B 1/0016* (2013.01); *A61B 1/00105* (2013.01);
(Continued)

(58) Field of Classification Search
CPC ............ A61B 1/00045; A61B 1/00052; A61B 1/00066; A61B 1/00112; A61B 1/00114;
(Continued)

(56) References Cited

U.S. PATENT DOCUMENTS

| 4,517,963 A | 5/1985 | Michel |
| 4,611,888 A * | 9/1986 | Prenovitz ............... A61B 1/042 348/75 |

(Continued)

FOREIGN PATENT DOCUMENTS

| DE | 19609034 A1 | 9/1996 |
| DE | 10081782 B4 | 9/2005 |
| DE | 102008049922 A1 | 4/2010 |

OTHER PUBLICATIONS

International Search Report & Written Opinion of the International Searching Authority Application No. PCT/DE2013/200010 dated: Aug. 15, 2013; dated: Aug. 22, 2013 8 pages.

*Primary Examiner* — Ryan Henderson
(74) *Attorney, Agent, or Firm* — Whitmyer IP Group LLC (57) ABSTRACT

A rotational device for rotating an endoscope having a stationary assembly, a rotatable assembly, which includes a distal coupling means for coupling to an endoscope, a drive means, which is embodied for putting the distal coupling means into rotational motion for rotating an endoscope connected to the distal coupling means, a proximal coupling means at the stationary assembly for coupling to a camera device, and an optical unit for transmitting light from the distal coupling means to the proximal coupling means.

20 Claims, 8 Drawing Sheets

(51) Int. Cl.
  *A61B 1/06* (2006.01)
  *G03B 17/48* (2006.01)
  *G02B 23/24* (2006.01)
  *A61B 1/05* (2006.01)

(52) U.S. Cl.
  CPC ...... *A61B 1/00128* (2013.01); *A61B 1/00131* (2013.01); *A61B 1/00147* (2013.01); *A61B 1/00183* (2013.01); *A61B 1/00195* (2013.01); *A61B 1/04* (2013.01); *A61B 1/042* (2013.01); *A61B 1/053* (2013.01); *G02B 23/2453* (2013.01); *G03B 17/48* (2013.01); *A61B 1/00066* (2013.01); *A61B 1/00126* (2013.01); *A61B 1/00179* (2013.01)

(58) Field of Classification Search
  CPC ........... A61B 1/00117; A61B 1/00121; A61B 1/00124; A61B 1/00126; A61B 1/00131; A61B 1/00133; A61B 1/0016; A61B 1/00195; A61B 1/04; A61B 1/042; A61B 1/00174; A61B 1/00177; A61B 1/00179; A61B 1/00181; A61B 1/00183; A61B 90/361; G02B 23/2453; G03B 17/48
  USPC ...... 600/109–112, 122, 160–180; 348/74–76
  See application file for complete search history.

(56) References Cited

U.S. PATENT DOCUMENTS

| | | | | |
|---|---|---|---|---|
| 5,515,478 | A * | 5/1996 | Wang | A61B 34/70 600/587 |
| 6,292,221 | B1 * | 9/2001 | Lichtman | G02B 23/2484 348/345 |
| 6,549,333 | B1 | 4/2003 | Nakatate et al. | |
| 6,932,760 | B1 | 8/2005 | Pang et al. | |
| 2005/0197533 | A1 * | 9/2005 | May | A61B 1/00071 600/164 |
| 2006/0206003 | A1 * | 9/2006 | Hoeg | A61B 1/00163 600/112 |
| 2006/0206006 | A1 * | 9/2006 | Schara | A61B 1/00177 600/173 |
| 2007/0213586 | A1 * | 9/2007 | Hirose | A61B 1/00105 600/112 |
| 2008/0300456 | A1 * | 12/2008 | Irion | A61B 1/00071 600/109 |
| 2009/0086213 | A1 * | 4/2009 | Masuda | A61B 5/0066 356/479 |
| 2010/0185212 | A1 | 7/2010 | Sholev | |
| 2011/0018988 | A1 | 1/2011 | Kazakevich et al. | |
| 2011/0175991 | A1 | 7/2011 | Hoeg et al. | |
| 2011/0288374 | A1 | 11/2011 | Hadani et al. | |
| 2012/0065470 | A1 | 3/2012 | Olds et al. | |

* cited by examiner

ROTATIONAL DEVICE AND METHOD FOR ROTATING AN ENDOSCOPE

FIELD OF THE INVENTION

The invention relates to a rotational device for rotating an endoscope and a method for rotating an endoscope by means of a rotational device.

BACKGROUND OF THE INVENTION

Such a rotational device comprises a rotatable assembly and a stationary assembly, and also a drive means. A distal coupling means for holding an endoscope is arranged at the rotatable assembly. The drive means is embodied to put the distal coupling means into rotational motion in order to rotate an endoscope connected to the distal coupling means.

A rotational device of the type described here can be used, in particular, for rotating a medical endoscope as is used, in particular, in micro-invasive operations on human or animal patients. Such an endoscope comprises a shaft, which is led to an operating site and, inter alia, serves to transmit light from the operating site to a camera device. The camera device registers the light and converts the latter into an analog or digital signal which is transmitted to a display device which images the operating site and therefore allows a surgeon to undertake a visual inspection of the operating site.

In the case of procedures performed micro-invasively, for example on the abdomen of a patient, a surgeon generally needs both hands to guide and operate instruments and, in this manner, perform the procedure. To date, an endoscope for optical registration and inspection of the operating site is usually held by a camera assistant, who stands e.g. behind or next to the surgeon. This may be disadvantageous because the movement space of the surgeon is restricted. Moreover, the camera assistant often needs to assume an ergonomically inexpedient body posture for a relatively long period of time, and so, with increasing operation duration, there may be blurring of the image as a result of the operation assistant tiring.

In order to make a camera assistant superfluous, holding systems, by means of which it is possible to statically assemble an endoscope on an operating table, are also used these days. Such holding systems use holding arms which have a relatively simple design and are universally usable, but only facilitate a manual change in the position of the endoscope by way of adjusting the holding arm.

In place of such holding systems, mechanical, in particular mechatronic guide systems, which facilitate a motor-driven adjustment of the position of an endoscope, are also known. By way of example, a guide system known from DE 196 09 034 A1 facilitates both the pivoting of an endoscope about a pivot point, which, in particular, corresponds to a penetration point at an abdominal wall of a patient or a different access opening at a patient, and the rotating of said endoscope about the longitudinal axis thereof.

In the guide system of DE 196 09 034 A1, this is facilitated by virtue of an adapter being attached at a housing of the endoscope, which adapter is coupled via a spur gear with a further spur gear of a drive device in such a way that the endoscope can be put into rotational motion, driven by the drive device. A camera device receiving light from the endoscope is held in a stationary manner in this case by virtue of the camera device being arranged at a holder holding the drive device by means of a retainer. Thus, the endoscope is rotated relative to the camera device.

The guide system as per DE 196 09 034 A1 facilitates a rotation of the endoscope about the longitudinal axis thereof and a corresponding setting of the field of view. By way of example, in the case of an endoscope which, by means of a suitable optical unit (a so-called "side-view tip"), receives light from a region lateral to the endoscope shaft, the fixed or adjustable direction of view of which endoscope is not parallel to the longitudinal axis of the endoscope shaft, the field of view can be pivoted by rotating the endoscope about the longitudinal axis thereof and an operating site can be observed from different observation directions.

However, as a result of an adapter having to be attached at the shaft of the endoscope in accordance with DE 196 09 034 A1, the usable length of the endoscope shaft which can be introduced into a patient is reduced. Moreover, the adapter comes into contact with the endoscope shaft, which is to be kept sterile for an operation, and so holding parts of the guide system for an operation also need to be sterilized (the sterilization is usually effected by autoclaving in an autoclave). Moreover, endoscopes from different producers, and also camera devices which can be used at an endoscope, may differ greatly in terms of the construction thereof. Therefore, under certain circumstances, it may not be possible to universally ensure the arrangement of both the endoscope and the camera device at the guide system for different endoscopes and camera devices.

SUMMARY OF THE INVENTION

An object of the present invention lies in providing an improved rotational device, an improved endoscope device and an improved method for rotating an endoscope which, in particular, enable a rotation of the endoscope about the longitudinal axis thereof in a simple manner which can be used as universally as possible in order to be able to change the field of view for inspecting an operating site.

This object is achieved by a rotational device for rotating an endoscope.

Embodiments of the present invention are based on the concept of providing, in a rotational device, a proximal coupling means arranged at a stationary assembly for coupling to a camera device, a distal coupling means at a rotatable assembly and an optical unit for transmitting light from the rotatable distal coupling means to the proximal coupling means.

Here, preferably either the stationary assembly or the rotatable assembly comprises a drive means for rotating the rotatable assembly relative to the stationary assembly. In particular, the drive means comprises an electric motor, an ultrasonic motor, a piezo-motor or any other motor.

Embodiments of the present invention proceed from the concept of developing a rotational device which, in the style of a modular assembly, is arranged between an endoscope and a camera device which is to be coupled to the endoscope and which registers light from the endoscope. To this end, the rotational device comprises a distal coupling means, which is embodied for the preferably non-destructively detachable mechanical connection to the endoscope, and a proximal coupling means, which is embodied for the preferably likewise non-destructively detachable mechanical connection to the camera device, such that the rotational device can be connected in a simple manner, firstly, to the endoscope and, secondly, to the camera device. By means of the optical unit, light is transmitted from the distal coupling means, i.e. from the endoscope, to the proximal coupling means, i.e. to the camera device. Light from the endoscope enters the rotational device at the distal coupling means, is transmitted by means of the optical unit and leaves the rotational device again at the proximal coupling means in order to be fed to the camera device.

The embodiment of the rotational device as an interposed modular assembly arranged between the endoscope and the camera device is facilitated, in particular, by the optical unit integrated into the rotational device. Here, the optical unit serves for transmitting light from the endoscope to the camera device and can comprise achromats, apochromats, rod lenses and other lenses, prisms or other light-forming, in particular light-refracting elements, but can also merely consist of one or more planar or curved cover slips, through which light passes through the rotational device.

The distal coupling means is, in particular, embodied for holding a proximal end of an endoscope. By way of example, the distal coupling means is embodied to hold an eyepiece of an endoscope. Such an eyepiece is, in particular, embodied pursuant to the German industrial standard DIN 58105 and comprises an external diameter of approximately 31.75 mm and an edge with a thickness of approximately 4.7 mm. The eyepiece can be held at the distal coupling means by means of holding claws, for example in a clamping, force-fit or frictionally engaged or interlocking manner. In an engagement state, the holding claws are brought into engagement with the edge of the eyepiece in order to hold the endoscope at the rotational device in a clamping, force-fit and/or frictionally engaged or interlocking manner. In order to detach the endoscope from the rotational device, the holding claws can be disengaged from the eyepiece-side end of the endoscope in order to lift the holding engagement with the eyepiece. Alternatively, the distal coupling means can be embodied for holding the proximal end of the endoscope, instead of the eyepiece, in a detachable force-fit and/or frictionally engaged or interlocking different manner.

What emerges from the distal coupling means being embodied for holding and fixing the proximal end of an endoscope, in particular the eyepiece of an endoscope, is, firstly, that the rotational device engages at the end of the endoscope supporting the eyepiece and hence at the proximal end of the endoscope. Therefore, the whole length of the endoscope shaft is available for guiding the endoscope to an operating site. Secondly, endoscopes generally use standardized eyepieces, and so a connection between the rotational device and a multiplicity of different endoscopes is made possible by the distal coupling means and hence a universal connection possibility for different endoscopes is provided.

The connection between the distal coupling means and the eyepiece of the endoscope is, in particular, embodied without slip or suitable for transmitting a torque, and so the endoscope is co-rotated without slip in the case of rotational motion of the distal coupling means.

The rotatable assembly is preferably mounted at the stationary assembly in a manner rotatable about a longitudinal axis of an endoscope connected to the rotational device in the intended state. By way of example, the endoscope can comprise a rigid shaft, which extends in the longitudinal direction and predetermines a longitudinal axis. In the case of an endoscope with a flexible shaft, the longitudinal axis means, in particular, the longitudinal axis of the proximal end of the shaft. The endoscope is connectable to the rotational device by means of the distal coupling means in such a way that, driven by the drive means, the rotatable assembly rotates about the longitudinal axis and therefore the endoscope can also be rotated about the longitudinal axis thereof in order, in this manner, to adjust the rotational position of the endoscope about the longitudinal axis.

The optical unit preferably transmits light, which is introduced into the rotational device by means of an endoscope, along the longitudinal axis from the distal coupling means to the proximal coupling means such that, at the proximal coupling means, the light can emerge and enter a camera device coupled to the proximal coupling means.

By way of example, the optical unit can comprise a first lens and a second lens offset along the longitudinal axis in relation to the first lens. In particular, the optical unit comprises a first achromat, a first lens, a second lens and a second achromat which are arranged in this sequence along the longitudinal axis, offset with respect to one another, in the optical beam path between the distal coupling means and the proximal coupling means. Light, which enters the optical unit from an endoscope at the distal coupling means, therefore initially passes through the first achromat, then the first lens, then the second lens and finally the second achromat, in order subsequently to be introduced into the camera device at the proximal coupling means. The first lens and the second lens can respectively be embodied as e.g. short lenses, rod lenses and/or, in turn, as achromatic lenses. A cover slip can additionally respectively be provided upstream of the first achromat and downstream of the second achromat (as viewed in the direction of the beam path) so as to protect the optical unit and lenses and achromats arranged therein against dirt and humidity. Alternatively, the first achromat and/or the second achromat can be embodied so as to fulfill the object of a cover slip.

Alternatively, an embodiment with other lens systems is possible, e.g. with four achromats and/or four non-achromatic lenses. Furthermore, a different number of achromats or other lenses may be provided.

In particular, an achromat comprises a combination of two or more lenses made of glasses or other transparent materials, the refractive indices of which depend on the wavelength in a different manner. The two or more lenses are embodied in such a way that the change in the back focus with the wavelength, which occurs in the individual lenses, is just balanced such that the change in the back focus with the wavelength for the whole achromat disappears for (at least) one wavelength. An achromat within the meaning of this invention also comprises an apochromat.

By way of example, the optical unit can be embodied in such a way that it generates an optical image at or in the vicinity of the proximal coupling means, which image substantially corresponds to the optical image which is provided at or near the distal coupling means by an endoscope. In particular the image near the distal coupling means and the image near the proximal coupling means are virtual images. The optical unit can therefore effect 1:1 imaging or 1:−1 imaging, i.e. imaging which substantially brings with it no change in the image size.

Alternatively, the optical unit is embodied for effecting a magnification or reduction in the image. Alternatively, the optical unit has a modifiable focal length or a modifiable focus. The focus and focal length can be set purely mechanically by means of operating wheels or operating sliders or the like. Alternatively or additionally, one or more (further) electric motors or other motors may be integrated, which facilitate motor-driven setting of focal length and/or focus.

The optical unit is preferably arranged in a cavity, e.g. a bore, of a shaft section of the stationary assembly and is therefore not co-rotated when the rotatable assembly rotates. In particular, the rotatable assembly is rotatably mounted about the shaft section of the stationary assembly, wherein provision can be made for one or more antifriction bearings, sliding bearings or other bearings for facilitating a smoothrunning motion of the rotatable assembly about the shaft section of the stationary assembly. The optical unit can preferably be encapsulated in the cavity of the shaft section of the stationary assembly in such a way that dirt and humidity cannot enter the optical unit and the optical unit is therefore protected. To this end, cover slips are provided in particular at both ends of the cavity, which cover slips can be embodied in a planar manner or as lenses and they are joined to the shaft section by soldering or in any other way such that they seal the cavity in a hermetically sealed manner.

In an alternative embodiment variant, the optical unit is arranged in or at the rotatable assembly, preferably likewise in an encapsulated manner in a cavity of a shaft section or of another component of the rotatable assembly.

In particular, the proximal coupling means of the rotational device is embodied as an eyepiece. Here, the eyepiece is preferably likewise embodied in accordance with the German industrial standard DIN 58105 and therefore standardized in terms of its design.

In an embodiment of the proximal coupling means as an eyepiece which is similar to the eyepiece of an endoscope to be connected to the distal coupling means, the rotational device can be switched as a modular, upgradable assembly between an endoscope and a camera device, without, to this end, structural modifications having to be made at the endoscope or the camera device. The endoscope can be connected in a simple manner to the distal coupling means by virtue of an eyepiece of the endoscope being clamped or fixed in any other way by means of holding claws of the distal coupling means. The camera device can be connected in a simple manner to the proximal coupling means in the form of the eyepiece. Here, the eyepiece of the rotational device can be clamped or fixed in any other way by a holding means of the camera device, which holding means is conventionally embodied to hold an eyepiece of an endoscope. The rotational device is therefore usable in a variable, universal manner, without an endoscope or a camera device needing to be adapted in a specific manner.

An endoscope device comprises a rotational device of the type described above, an endoscope connected to the distal coupling means of the rotational device and a camera device connected to the proximal coupling means of the rotational device. Here, the endoscope can preferably comprise a shaft and a swivel prism which is swivelable about a swivel axis and arranged at a distal end distant from the rotational device. The swivel axis of the swivel prism is not parallel but, in particular, orthogonal to the longitudinal axis of the endoscope. The swivel prism can be swiveled about the swivel axis thereof, for example by means of a motor integrated into the endoscope, in order, in this manner, to be able to modify in a variable manner a field of view looking in particular laterally out of the shaft of the endoscope. As a result of, firstly, the swivel prism being able to be swiveled and, secondly, the shaft of the endoscope being able to be rotated about the longitudinal axis thereof by means of the rotational device, it is possible, in an advantageous manner, to visually inspect an operating site over a large region.

In order to control the rotational device and in order to control the swivel prism, provision can be made, for example, for unified control electronics, by means of which the rotational position of the shaft and the position of the swivel prism can be set in a variable manner. Alternatively, different control electronics can be provided for, firstly, the rotational device and, secondly, the swivel prism.

By way of example, the endoscope device comprising the endoscope, the rotational device and the camera device can be held at an operating table by virtue of a holder engaging at the rotational device and also holding the endoscope and the camera device via the rotational device.

A rotational device of the type described here can be combined with a guide system, in which the position of an endoscope in space can be set in a variable manner by moving a holding arm. Rotating the endoscope by means of the rotational device can achieve simple setting of the field of view, also in the case of those guide systems, in particular when using so-called side-view endoscopes, which have a field of view directed laterally from the endoscope shaft. When combining a guide system with a rotational device, the use of a side-view tip can achieve an enlargement of the overall visible field of view compared to conventional guide systems.

The object is also achieved by a method for rotating an endoscope by means of a rotational device, in which an endoscope is connected at a distal coupling means of a rotatable assembly and a drive means puts the distal coupling means into rotational motion for rotating the endoscope connected to the distal coupling means. Here, provision is made for a camera device to be connected at a proximal coupling means of a stationary assembly and for an optical unit to transmit light from the distal coupling means to the proximal coupling means.

Here, in principle, the stationary or the rotatable assembly may comprise the drive means.

The advantages and advantageous embodiments described above for the rotational device analogously also find application in the method.

BRIEF DESCRIPTION OF THE DRAWINGS

The concept underlying the invention will be explained in more detail below on the basis of the exemplary embodiments depicted in the figures. In detail.

DETAILED DESCRIPTION OF THE INVENTION

Figure 1:
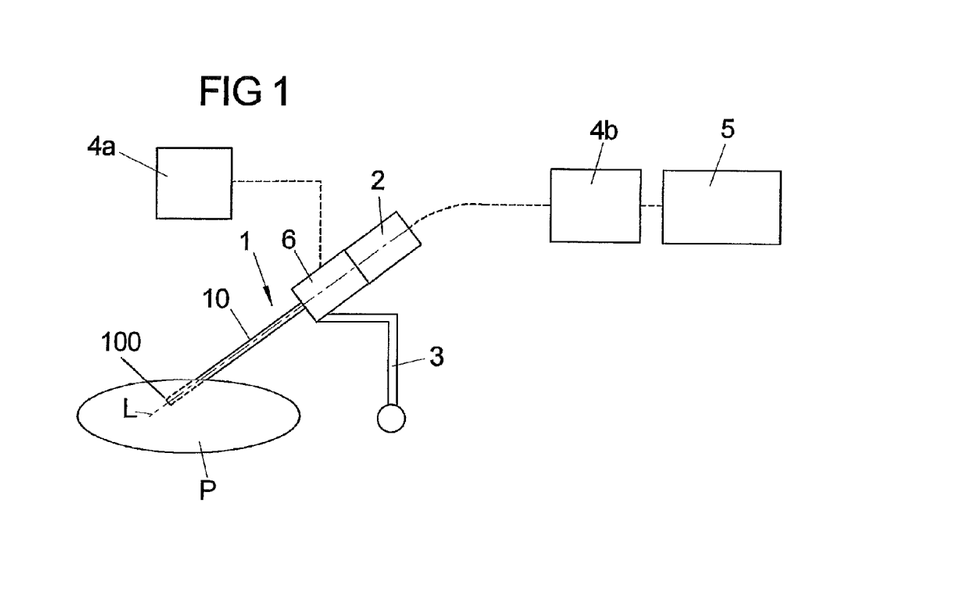
FIG. 1 shows a schematic illustration of an endoscope device.

FIG. 1 shows a schematic illustration of an endoscope device comprising an endoscope 1 and, connected thereto, a camera device 2 serving for recording or registering images from an operating site at a patient P. The endoscope 1 comprises a shaft 10 with a longitudinal axis L, the distal end 100 of which is guided to the patient P and inserted into the patient P. Light from the operating site can be guided to the camera device 2 via the shaft 10 of the endoscope 1, said camera device converting the light into analog or digital and, in particular, electrical signals and feeding these to an evaluation unit 4b. The evaluation unit 4b processes the signals. The processed signals are transmitted to a display device 5 in the form of a monitor for displaying images of the operating site.

A holder 3 is fastened at e.g. an operating table. The holder 3 holds a rotational device 6 which mechanically and optically couples the endoscope 1 to the camera device 2. The rotational device 6 facilitates a rotation of the endoscope 1 about the longitudinal axis L of the shaft 10 and, in this manner, a variation, in particular a swiveling, of a field of view of the endoscope 1.

A control unit 4a serves for controlling the rotational device 6. The control unit 4a and the evaluation unit 4b can be, deviating from the illustration in FIG. 1, coupled for interchanging signals or combined mechanically and/or functionally to form a unit.

Figure 2:
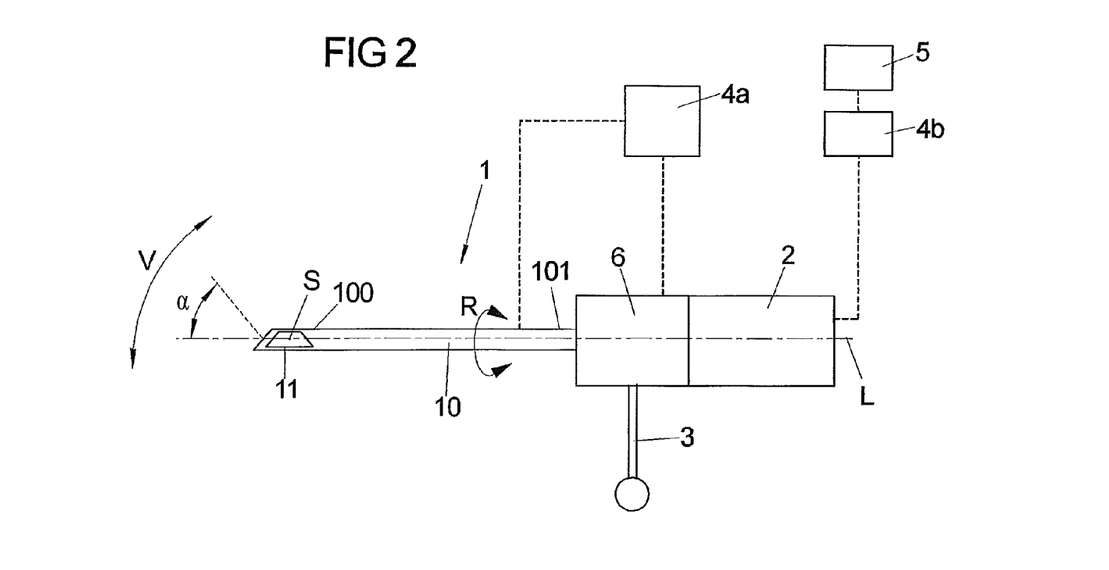
FIG. 2 shows a schematic illustration of a further endoscope device.

FIG. 2 shows a schematic illustration of a further endoscope device which, in terms of some features and properties, is similar to the endoscope device depicted above on the basis of FIG. 1. The following illustrates in particular features and properties in which the endoscope device from FIG. 2 differs from the endoscope device from FIG. 1.

In the endoscope device depicted in FIG. 2, the endoscope 1 comprises a swivel prism 11 (may also be referred to as a pivotable prism) at its distal end 100. The swivel prism 11 is swivelable about a swivel axis S, for example by means of a motor integrated into the endoscope, by means of a push or pressure rod, or in any other way. The swivel axis S is orthogonal to the longitudinal axis L of the shaft 10 and orthogonal to the plane of the drawing in FIG. 2. The swivel prism 11 can be used to register light from an in particular conical field of view which is describable by a viewing angle α. By swiveling the swivel prism 11 about the swivel axis S (swivel movement V), it is possible to vary the field of view, in particular to swivel it in a plane perpendicular to the swivel axis S. By rotating the endoscope 1 by means of the rotational device 6, it is additionally also possible to rotate the field of view about the longitudinal axis L (rotational motion R) such that an operating site can be observed in a large spatial region by, firstly, swiveling the swivel prism 11 and, secondly, rotating the shaft 10 of the endoscope 1.

As an alternative to using a swivel prism, the direction of view can be swiveled in a different manner, e.g. by means of an arrangement of reflecting surfaces known from periscopes or by mechanical angling of the endoscope tip. The use of a side-view endoscope with a defined field of view is likewise possible.

The proximal end 101 of the endoscope 1 is rigidly connected to the rotational device 6. The rotational device 6 is in turn mechanically connected to the camera device 2. The endoscope device is held in its position by the holder 3 engaging at the rotational device 6.

For interchanging electrical or other signals and for transmitting power, the camera device 2 is coupled to the evaluation unit 4b. For interchanging electrical or other signals and for transmitting power, the rotational device 6, and optionally the endoscope 1, are coupled to the control unit 4a. The evaluation unit 4b serves to receive and evaluate signals from the camera device 2 and feed said signals to the display device 5. At the same time, the control unit 4a can control the rotational device 6 and optionally also the swivel prism 11 in order in this way to set and modify the rotational position of the shaft 10 and the position of the swivel prism 11.

Figure 3:
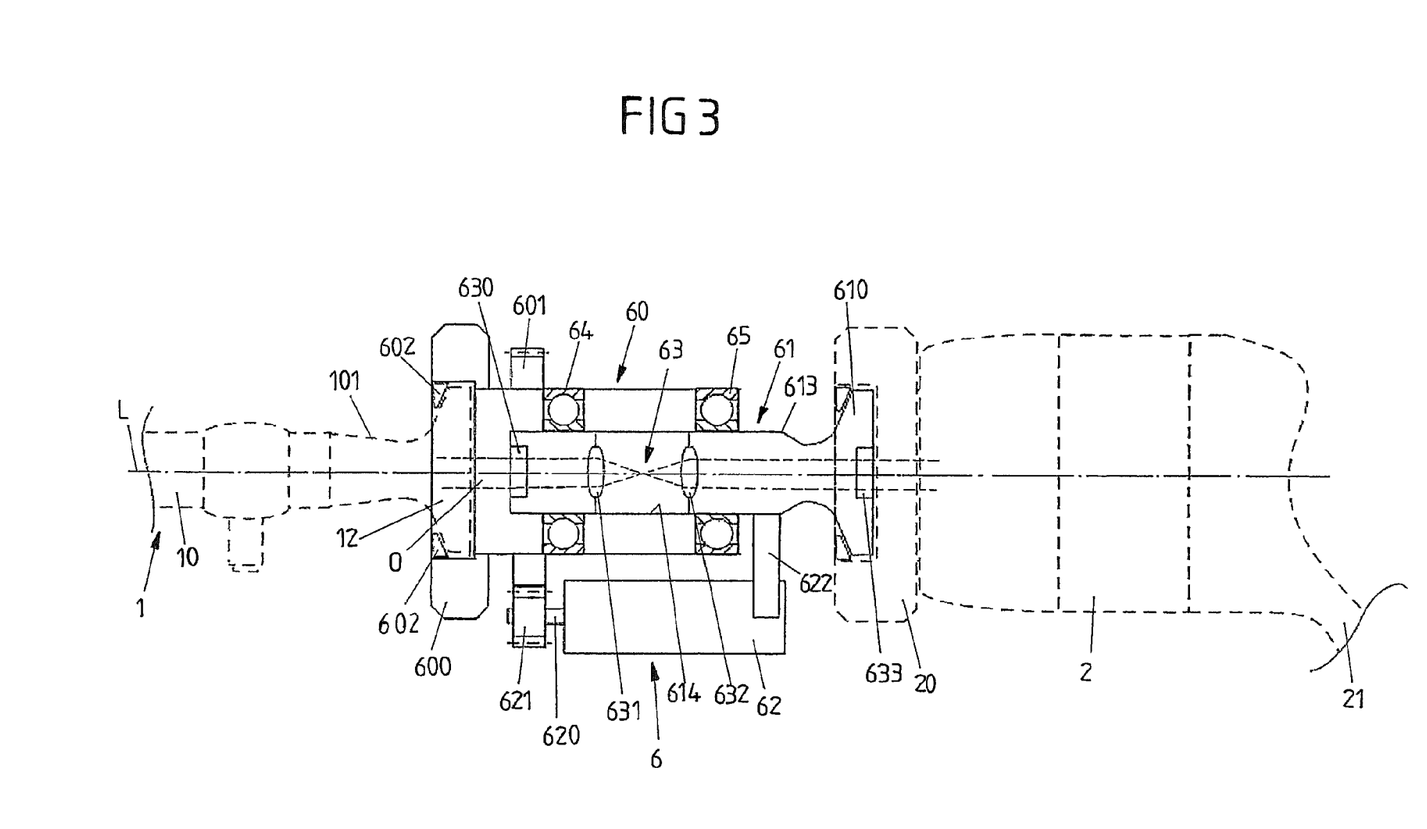
FIG. 3 shows a schematic sectional illustration of a rotational device for rotating an endoscope connected to a rotatable assembly of the rotational device.

FIG. 3 shows a schematic sectional illustration of a rotational device 6 using solid lines and of an endoscope 1 and a camera device 2 using dashed lines. The sectional plane in FIG. 3 contains the longitudinal axis L of the shaft 10 of the endoscope 1. The rotational device 6, the endoscope 1 and the camera device 2 can comprise features and properties which are similar to the ones depicted above on the basis of FIGS. 1 and 2. In particular, the rotational device 6 depicted in FIG. 3 is one of the rotational devices depicted above on the basis of FIGS. 1 and 2.

The rotational device 6 comprises a stationary assembly 61, at which a rotatable assembly 60 is arranged in a manner rotatable about the longitudinal axis L by means of bearings 64, 65. The bearings 64, 65 are, in particular, embodied as ball bearings. The stationary assembly 61 has a shaft section 613, at the proximal end of which facing the camera device 2 a proximal coupling means 610 in the form of an eyepiece is arranged. The rotatable assembly 60 comprises a distal coupling means 600, which is embodied for mechanically coupling to an eyepiece 12 (may also be referred to as the cup of an eyepiece) of the endoscope 1.

The proximal coupling means 610 of the stationary assembly 61 and the eyepiece 12 of the endoscope 1 have a similar or the same form and are preferably embodied in accordance with the German industrial standard 58105 (as of June 2000) and are therefore standardized.

The proximal coupling means 610 of the stationary assembly 61 is connectable to a coupling means 20 of the camera device 2 in a clamping, force-fit and/or frictionally engaged or interlocking manner. The coupling means 20 of the camera device 2 can have a similar or the same design as the coupling means 600 of the rotational device 6 and e.g. comprise holding claws for the clamping, force-fit and/or frictionally engaged or interlocking hold of the proximal coupling means 610.

The distal coupling means 600 of the rotatable assembly 60 comprises holding claws 602, by means of which the eyepiece 12 of the endoscope 1 can be connected to the rotational device 6 in a clamping, force-fit and/or frictionally engaged or interlocking manner. Here, in a state, in which the endoscope 1 is arranged at the rotational device 6, the holding claws 602 engage with the eyepiece 12 in a clamping, force-fit and/or frictionally engaged or interlocking manner. In order to release the endoscope 1, the holding claws 602 can be brought out of engagement with the eyepiece 12 such that the endoscope 1 can be separated from the rotational device 6.

In a state in which it is connected to the distal coupling means 600 of the rotatable assembly 60 of the rotational device 6, the endoscope 1 extends along the longitudinal axis L and it is rotatable about the longitudinal axis L by rotating the rotatable assembly 60. Here, the rotational device 6 engages at the eyepiece 12 arranged at the proximal end 101 of the shaft 10, and therefore right at the proximal end 101 of the endoscope 1, and so the complete length of the shaft 10 is available for guiding the endoscope 1 to an operating site.

A drive means 62 in the form of an electric motor, which engages with a gearwheel 601 at the rotatable assembly 60 via a pinion 621 arranged on a driveshaft 620, is arranged at the stationary assembly 61 via a connecting piece 622. The gearwheel 601 is securely arranged at the rotatable assembly 60 in such a way that, driven by the pinion 621 of the drive means 62, the gearwheel 601, and therefore the rotatable assembly 60, can be put into rotational motion about the longitudinal axis L in order, in this manner, to modify the rotational position of the endoscope 1 about the longitudinal axis L.

Arranged in a bore 614 of the shaft section 613 of the stationary assembly 61 is an optical unit 63 which as seen in the direction of the beam path from the endoscope 1 to the camera device 2 comprises a first cover slip 630, a first lens 631, a second lens 632 and a second cover slip 633. Light O enters the optical unit 63 from the endoscope 1 through the first cover slip 630, passes through the lenses 631, 632, re-exits the optical unit 63 through the second cover slip 633 and reaches into the camera device 2.

By way of example, the optical unit 63 can bring about 1:−1 imaging, in particular provide a virtual image near the cover slip 633 which corresponds to a virtual image provided by the endoscope 1 near the cover slip 630. What should be understood by this is that the optical image has substantially not been changed in terms of size and form, i.e. it is neither magnified nor distorted, but it is rotated by 180 degrees.

An erect image or an image without side reversal or rotation, e.g. a 1:1 image, can be generated by a different design of the optical unit 63.

By means of the rotational device 6, a modular assembly is provided which can be inserted between the endoscope 1 and the camera device 2, without this requiring structural changes at the endoscope 1 or the camera device 2. By means of the distal coupling means 600 at the rotatable assembly 60 and the proximal coupling means 620 in the form of the eyepiece at the stationary assembly 610, standardized connectors are provided which can be connected universally, firstly, to the eyepiece 12 of an endoscope 1 and, secondly, to a coupling means 20, embodied for coupling to an eyepiece, of a camera device 2.

As depicted in FIG. 3, the camera device 2 comprises a connector 21, by means of which, for example, an electric or optical connection can be established with the evaluation unit 4*b* for transmitting an image signal.

Figure 4:
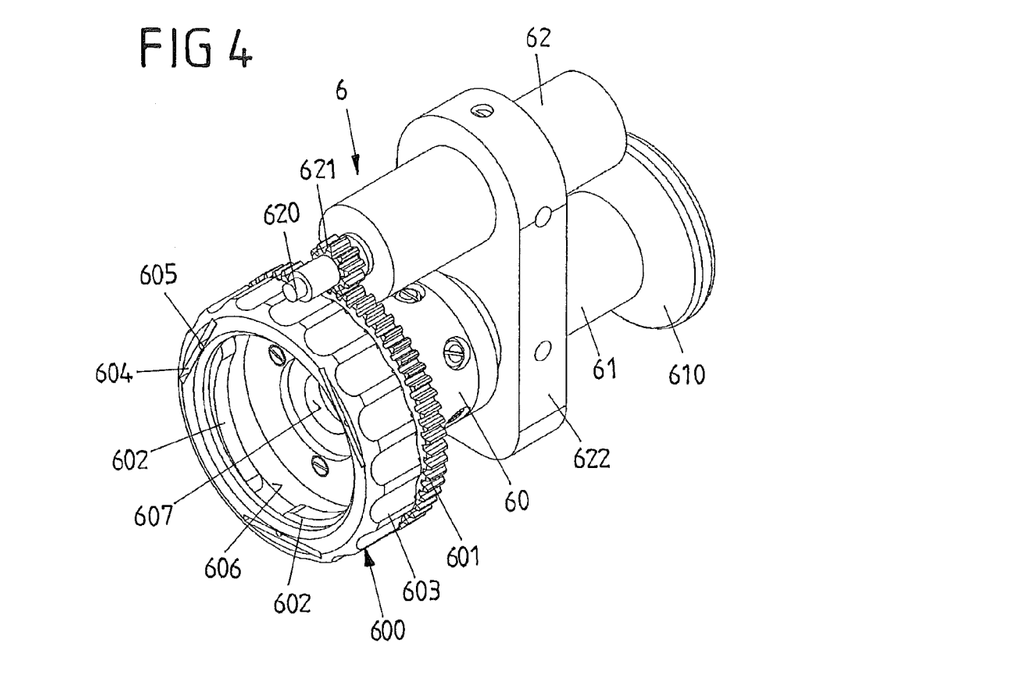
FIG. 4 shows a schematic axonometric illustration of an exemplary embodiment of a rotational device.
Figure 5A:
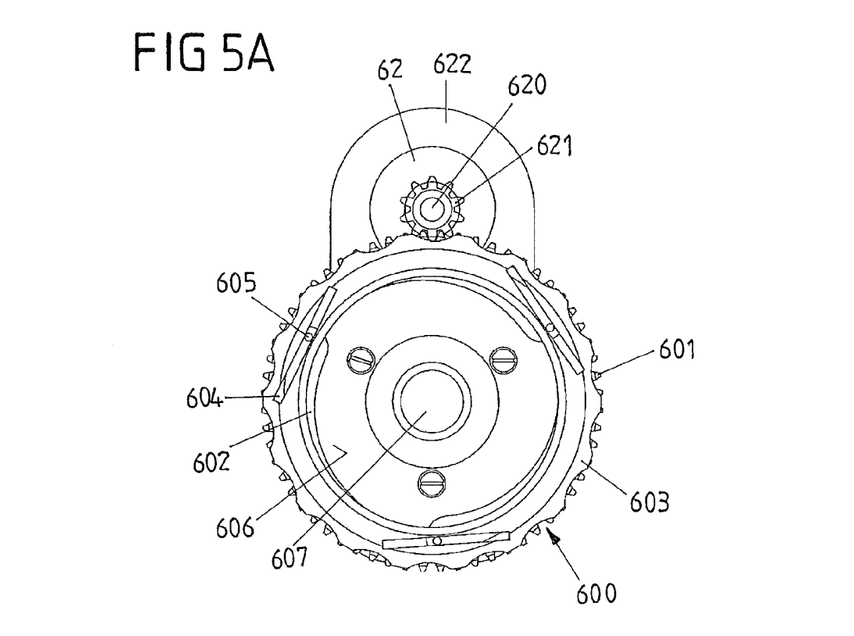
FIG. 5A shows a further schematic illustration of the rotational device from FIG. 4.
Figure 5B:
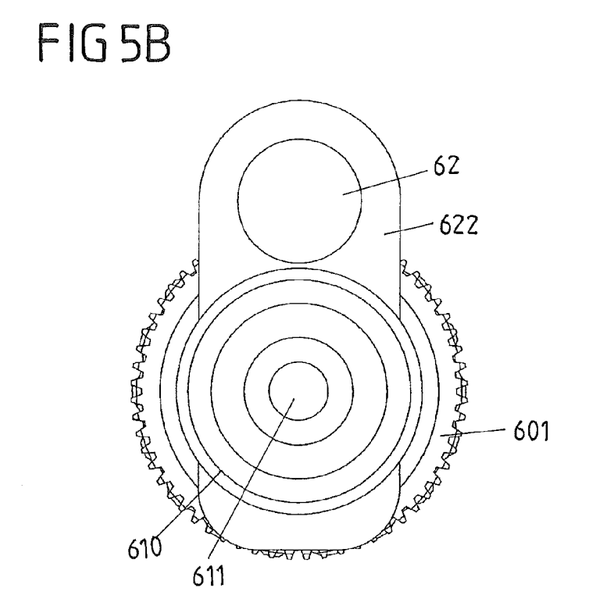
FIG. 5B shows a further schematic illustration of the rotational device from FIGS. 4 and 5A.
Figure 5C:
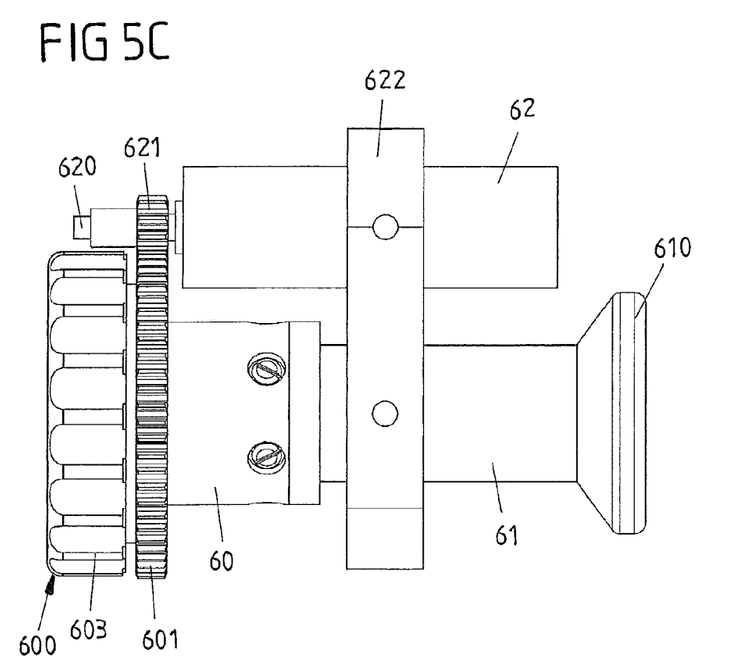
FIG. 5C shows a further schematic illustration of the rotational device from FIGS. 4 to 5B.
Figure 5D:
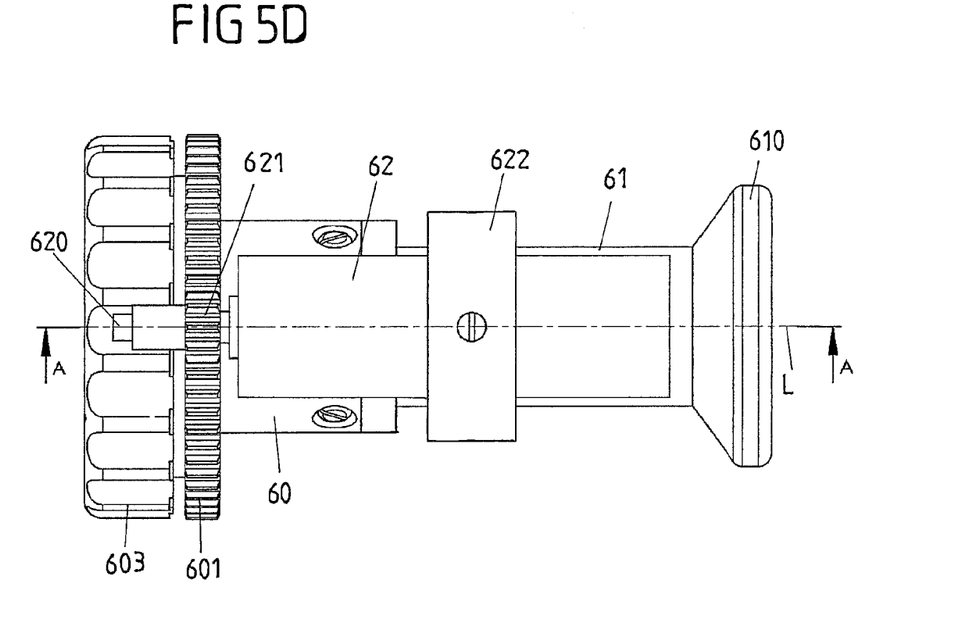
FIG. 5D shows a further schematic illustration of the rotational device from FIGS. 4 to 5C.
Figure 6:
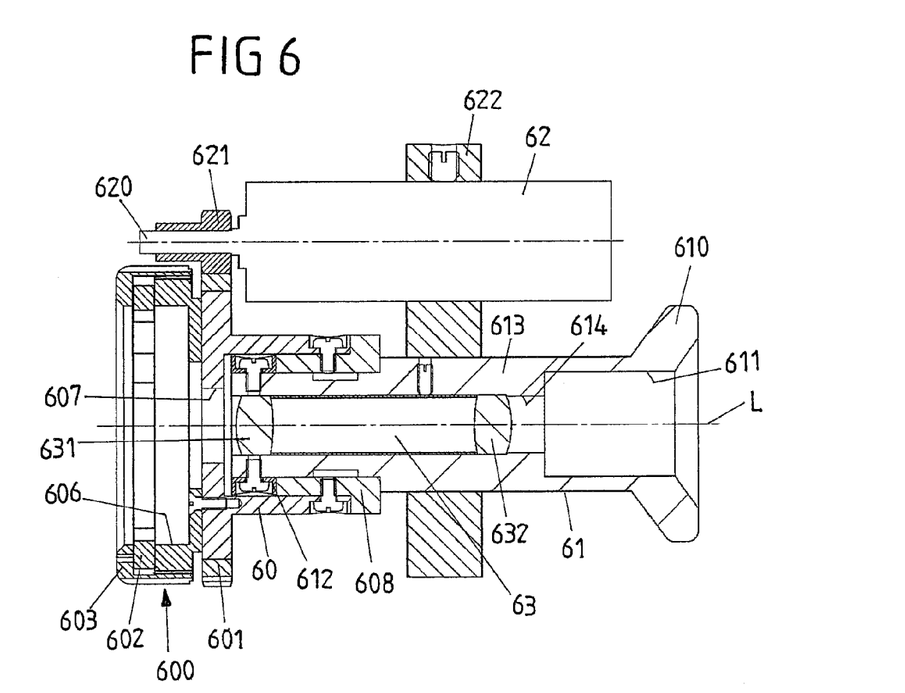
FIG. 6 shows a schematic sectional illustration of the rotational device from FIGS. 4 to 5D.

FIGS. 4 to 6 show schematic illustrations of an exemplary embodiment of a rotational device 6, which, in terms of some features and properties, is similar to the rotational device depicted above on the basis of FIGS. 1 to 3. The following illustrates, in particular, features and properties in which the rotational device 6 from FIGS. 4 to 6 differs from the one depicted above on the basis of FIGS. 1 to 3. Here, FIG. 4 shows an axonometric illustration of the rotational device 6, FIGS. 5A to 5D show views from the front (FIG. 5A), from behind (FIG. 5B), from the side (FIG. 5C) and from above (FIG. 5D). FIG. 6 shows an illustration of a section through the rotational device 6 along the plane A-A indicated in FIG. 5D.

The rotational device 6 comprises a stationary assembly 61, which supports a drive means 62 by means of a connecting piece 622 and which is, for example, rigidly assembled on a holder 3 (cf. FIGS. 1 and 2). At the stationary assembly 61, a rotatable assembly 60 is arranged rotatably about a longitudinal axis L via a bearing section 608. The rotatable assembly 60 engages in a meshing manner with a pinion 621 arranged at a driveshaft 620 of the drive means 62 via a gearwheel 601. The bearing section 608 is mounted at a shaft section 613 in a manner sliding about the longitudinal axis L in the circumferential direction and fixed at the shaft 613 in an interlocking manner by means of a holding ring 612 such that the rotatable assembly 60 is held axially at the stationary assembly 61. The bearing section 608 is detachably connected to other parts of the rotatable assembly 60 in particular by means of one or more screws. The holding ring 612 is detachably connected to the shaft section 613, in particular by means of one or more screws.

The rotatable assembly 60 comprises a distal coupling means 600, which is formed by a base section 606, a handwheel 603 arranged thereon and holding claws 602 arranged adjustably at the base section 606. The distal coupling means 600 serves for the detachable mechanical coupling to an eyepiece 12 of an endoscope 1 (cf. e.g. FIGS. 1 to 3). When the endoscope 1 is placed thereon, the distal coupling means 600 holds the eyepiece 12 at the rotatable assembly 60 in a clamping, force-fit and/or frictionally engaged or interlocking manner by means of the holding claws 602 such that the endoscope 1, together with the rotatable assembly 60, can be moved without slip.

Each holding claw 602 engages via a pin 605 with an assigned guide rail 604 on the handwheel 603. As a result, rotational motion of the handwheel 603 relative to the base part 606 is accompanied with an at least partly radial movement of the holding claws 602 between radially inner-lying positions, where there is engagement with the eyepiece 12 of an endoscope 1, and radially outer-lying positions without engagement.

At the stationary assembly 61, a proximal coupling means 610 in the form of an eyepiece is provided at a proximal end of the shaft section 613 distant from the rotatable assembly 60, which proximal coupling means can be detachably connected to a camera device 2 (cf. FIGS. 1 to 3) or a user can peer therethrough into the endoscope 1.

An optical unit 63, which is substantially formed by lenses 631, 632, is arranged in a bore 614 of the shaft section 613 of the stationary assembly 61, which bore extends along the longitudinal axis L and, in particular, is rotationally symmetric thereto. Light can enter the optical unit 63 through an opening 607 at the rotatable assembly, pass through the optical unit 63 and reemerge at an opening 611 of the stationary assembly 61 in order to be guided to a camera device 2 connected to the proximal coupling means 610.

The rotational device 6 implements a modular assembly which can be connected to an endoscope 1 by means of the distal coupling means 600 and to a camera device 2 by means of the proximal coupling means 610. The distal coupling means 600 is embodied for coupling to a standardized eyepiece 12 of an endoscope 1 and the proximal coupling means 610 has the shape of a likewise standardized eyepiece. Therefore, the rotational device 6 can be connected universally to conventional endoscopes 1 and camera devices 2, without an adaptation of the endoscope 1 or the camera device 2 being necessary.

An endoscope 1 can be rotated about the longitudinal axis L by means of the rotational device 6, wherein the endoscope 1 extends along the longitudinal axis L with its shaft 10 when it is connected to the rotatable assembly 60 in a clamping, force-fit and/or frictionally engaged or interlocking manner by way of the first coupling means 600.

Figure 7:
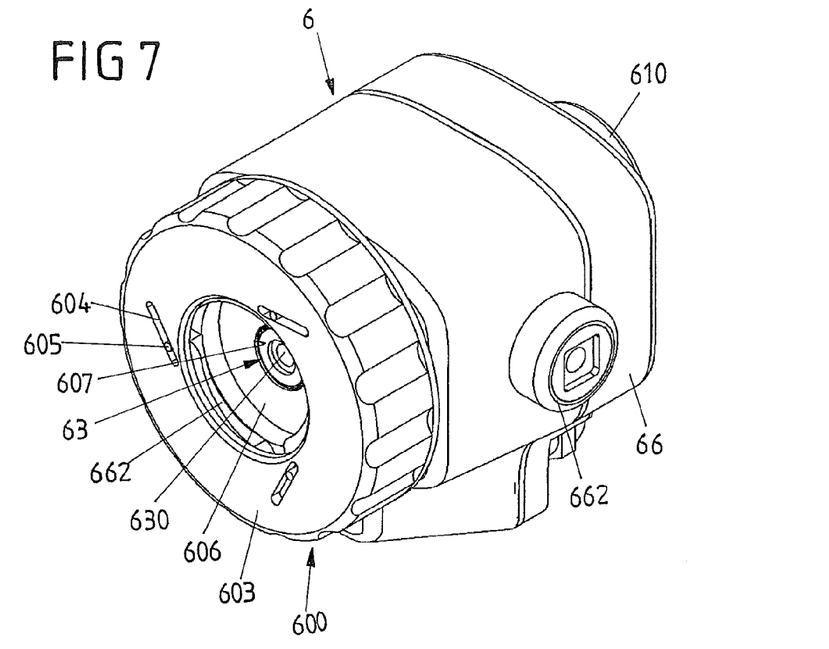
FIG. 7 shows a schematic axonometric illustration of a further rotational device.
Figure 8A:
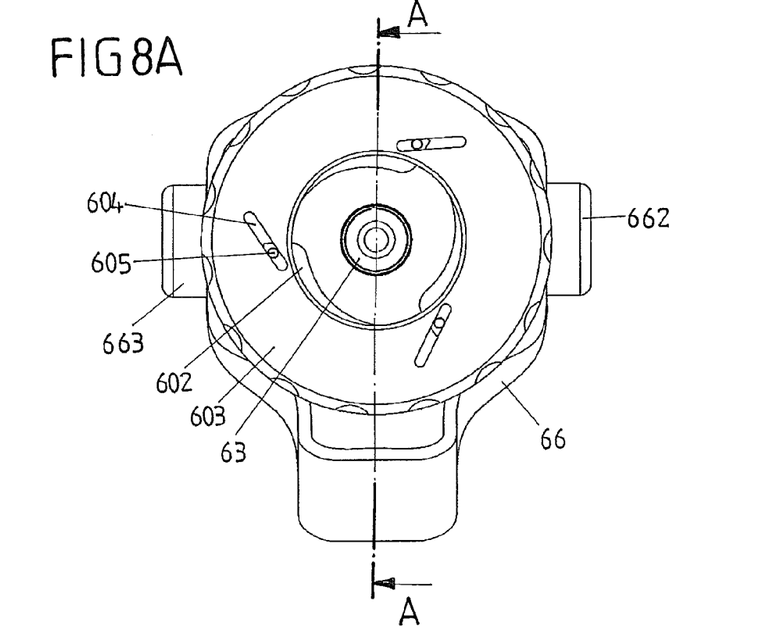
FIG. 8A shows a further schematic illustration of the rotational device from FIG. 7.
Figure 8B:
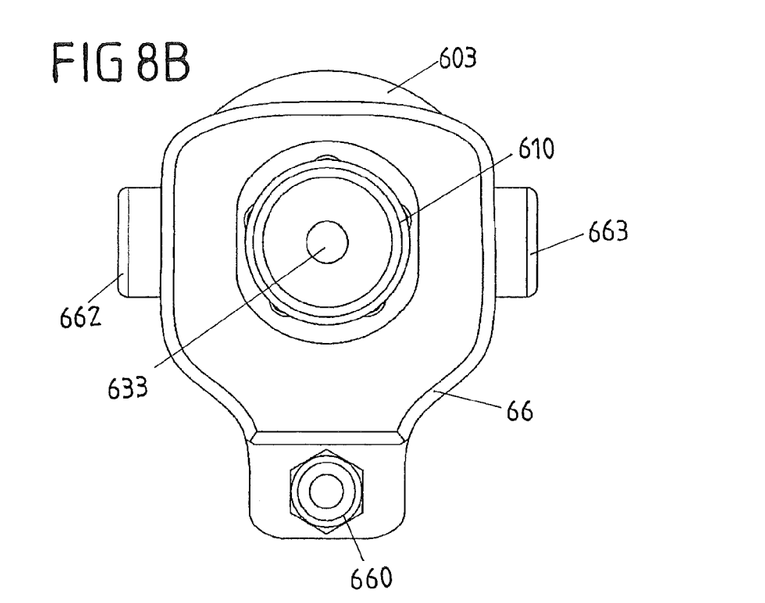
FIG. 8B shows a further schematic illustration of the rotational device from FIGS. 7 and 8A.
Figure 8C:
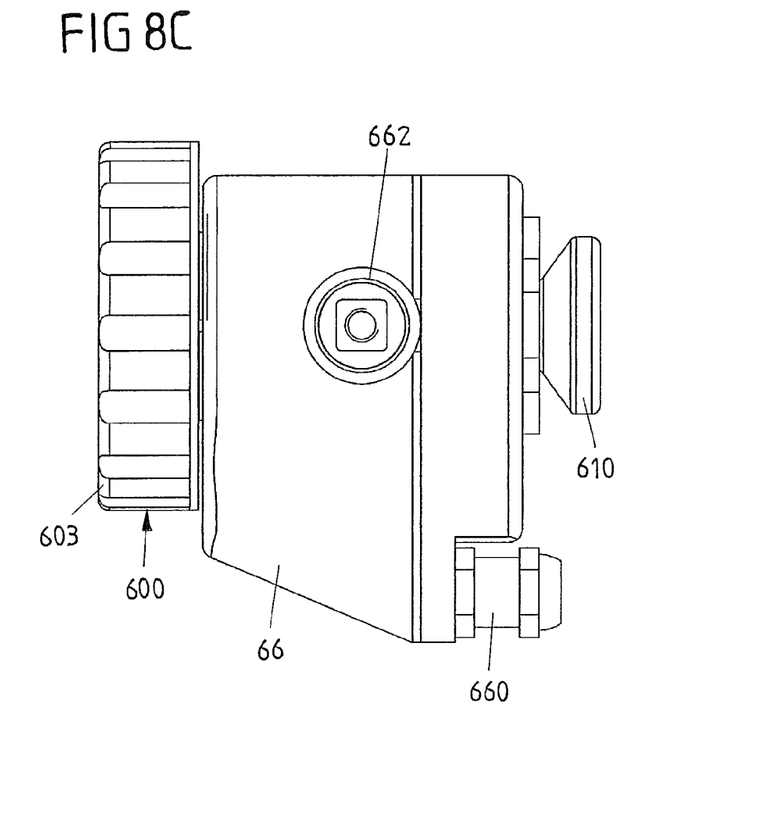
FIG. 8C shows a further schematic illustration of the rotational device from FIGS. 7 to 8B.
Figure 9:
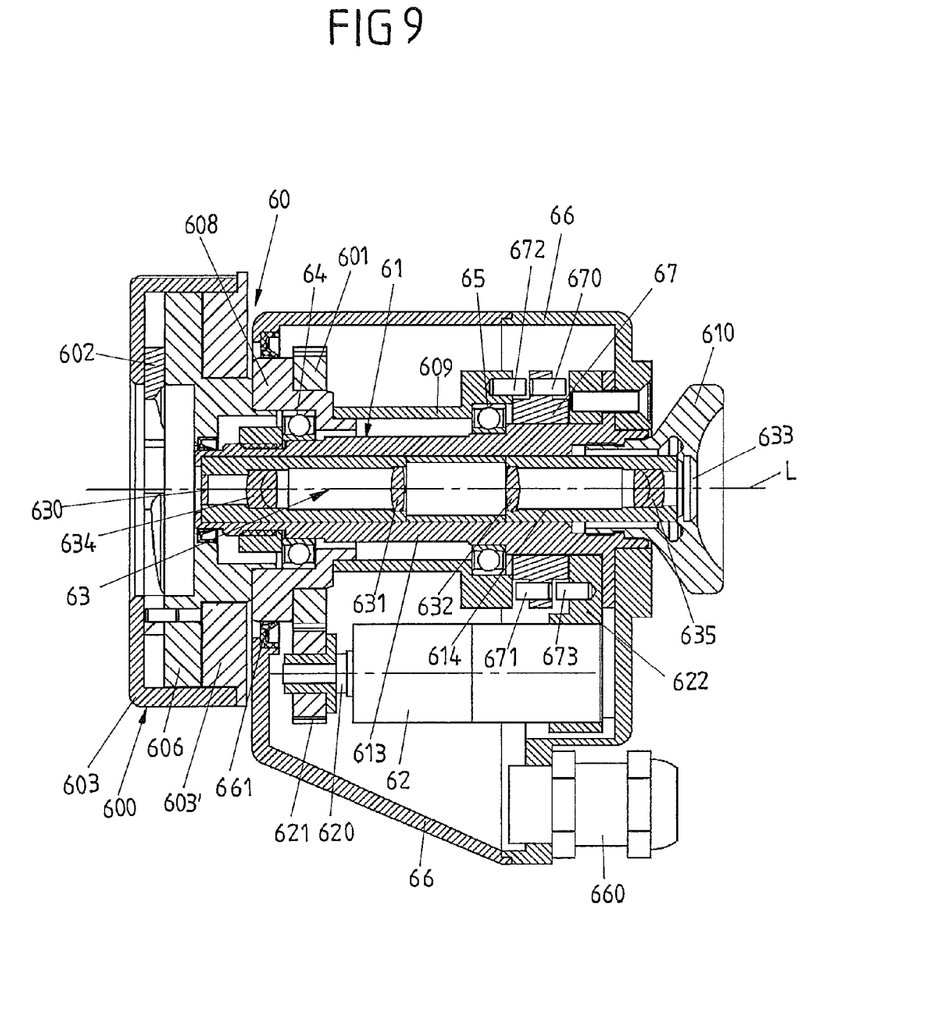
FIG. 9 shows a schematic sectional illustration of the rotational device from FIGS. 7 to 8C.

FIGS. 7 to 9 show schematic illustrations of an exemplary embodiment of a rotational device 6 which, in terms of some features and properties, is similar to the rotational devices depicted above on the basis of FIGS. 1 to 6. The following illustrates, in particular, features and properties in which the rotational device 6 from FIGS. 7 to 9 differs from the one depicted above on the basis of FIGS. 1 to 3. FIG. 7 shows an axonometric view, FIG. 8A shows a view from the front, FIG. 8B shows a view from behind, FIG. 8C shows a view from the side and FIG. 9 shows an illustration of a section along the plane A-A indicated in FIG. 8A.

The rotational device 6 depicted in FIGS. 7 to 9, like the rotational devices depicted above on the basis of FIGS. 1 to 6, comprises a stationary assembly 61, a rotatable assembly 60, an optical unit 63 and a drive means 62. The rotatable assembly 60 is mounted in a rotatable manner at the stationary assembly 61 by means of two bearings 64, 65. The bearings 64, 65 are arranged between a shaft section 613 of the stationary assembly 61 and bearing sections 608, 609 at the rotatable assembly 60. A gearwheel 601 is rigidly arranged at the bearing section 608, said gearwheel being in meshing engagement with a pinion 621 at a driveshaft 620 of the drive means 62. As a result, a rotation of the pinion 621 generated by the drive means 62 causes rotational motion of the gearwheel 601 and of the rotatable assembly 60.

Deviating from the illustration on the basis of FIGS. 7 to 9, a drive means for a rotational device according to the invention may have an alternatively embodied gearing or be coupled thereto. By way of example, the gearing is a worm gear or a chain gear.

Deviating from the illustration on the basis of FIGS. 7 to 9, provision can be made for a drive means without a gearing. By way of example, such a drive means may comprise a so-called hollow rotor motor or a piezo-motor or ultrasonic motor which, in particular, is arranged symmetrically in relation to the longitudinal axis L or coaxially to the shaft section 613 of the stationary assembly 61, to the bore 614 and to the bearing sections 608, 609.

The rotatable assembly 60 comprises a distal coupling means 600, which is formed by a base part 606, a handwheel 603 and holding claws 602. Similar to what was described above on the basis of FIGS. 4 to 6, the holding claws 602 serve for a clamping, force-fit and/or frictionally engaged or interlocking hold of an eyepiece 12 of an endoscope. By rotating the handwheel 603 relative to the base part 606, the holding claws 602 can be moved radially inward and, as a result of that, come into engagement with an eyepiece 12 in a clamping, force-fit and/or frictionally engaged or interlocking manner or, for releasing the eyepiece 12, they can be moved radially outward and therefore come out of engagement with the eyepiece 12. The handwheel 603 is fixedly connected to a holding ring 603' and, with the holding ring 603', engages around the base part 606 such that the handwheel 603 is not axially movable relative to the base part 606.

The optical unit 63 of the stationary assembly 61 has, as viewed along the beam path from the distal coupling means 600 to the proximal coupling means 610, a cover slip 630, a first achromat 634, a first single lens 631, a second single lens 632, a second achromat 635 and a further cover slip 633. The optical unit 63 guides light from an endoscope 1 connected to the distal coupling means 600 to the proximal coupling means 610 and to a camera device 2, which is connected to the proximal coupling means 610.

In particular, the optical unit 63 brings about 1:1 imaging or 1:−1 imaging of the image received by the endoscope 1 within the meaning of what was described above on the basis of FIG. 3 and therefore does not distort or magnify the image.

The optical unit 63 is arranged in a bore 614 of the shaft section 613, which bore is rotationally symmetric in relation to the longitudinal axis L. The optical unit 63 is encapsulated, in particular hermetically encapsulated in the bore 614 by means of the cover slips 630, 633 and therefore protected against humidity and dirt.

The rotational device 6 depicted on the basis of FIGS. 7 to 9 comprises a housing 66, which is securely connected to the stationary assembly 61 and, via a sealing ring 661, abuts in a sealing manner at an outer lateral surface of the bearing section 608. In particular, the housing 66 encapsulates the stationary assembly 61 with the drive means 62 arranged thereon and therefore protects it from humidity and dirt.

As depicted in FIGS. 7 to 8C, connectors 662, 663 are attached at the housing 66, by means of which connectors a holder 3 can be fixed at the rotational device 6, for example screwed to the rotational device 6. Moreover, a connector 660, by means of which an electrical cable can be guided to the drive means 62 in order to supply the drive means 62 with power and control the latter, is provided on the housing 66. In particular, the connector 660 is embodied as a cable leadthrough with strain relief which is sealed off with respect to fluids or as an electrical and/or optical plug-in connector.

Furthermore, a rotatable intermediate ring 67, which comprises stops 670, 671, is arranged at the shaft section 613 of the stationary assembly 61. Together with, firstly, a stop 672 at the bearing section 609 of the rotatable assembly 60 and, secondly, together with the stop 673 at the connecting piece 622 of the stationary assembly 61, the stops 670, 671 restrict the swivel angle of the rotatable assembly 60 relative to the stationary assembly 61. Here, the intermediate ring 67 itself is mounted in a rotatable manner at the shaft section 613 and can, in sections, be moved together with the rotatable assembly 60 when the stop 672 of the rotatable assembly 60 abuts against the stop 671 of the intermediate ring 67 until the stop 670 of the intermediate ring 67 impacts at the stop 673 of the stationary assembly. Depending on arrangement and design of the stops 670, 671, 672 and 673, and by means of the intermediate ring 67, the rotational path of the rotatable assembly 60 relative to the stationary assembly 61 can be restricted to a rotational angle of approximately 360 degrees or approximately 720 degrees or to a larger or smaller rotational angle. By restricting the rotational path, it is possible to avoid an optical waveguide winding up at the endoscope 1 and/or facilitate the calibration of the motor position or the rotational position of the rotatable assembly.

The rotational device 6 depicted on the basis of FIGS. 7 to 9 is also provided as a modular assembly which can be connected firstly to an endoscope 1 and secondly to a camera device 2. The rotational device 6 can be arranged in a universal manner between an endoscope 1 having a standardized eyepiece 12 and a camera device 2 embodied for the connection to an eyepiece 610. Therefore, the rotational device 6 can readily be updated in existing endoscope devices.

The concept underlying the invention is not restricted to the exemplary embodiments described above, but it can also be implemented in embodiments of a completely different nature.

In particular, a rotational device of the type described here is not necessarily restricted to medical use, but can also be used in endoscope devices in other fields, for example in the field of technical endoscopy for material testing or production control.

The optical unit of the rotational device need not have 1:1 imaging or 1:−1 imaging but can also act in a magnifying or reducing manner. Alternatively, the optical unit can be embodied in an adjustable manner by virtue of individual lenses being movable along the longitudinal axis such that e.g. a zoom setting or a focus setting can also be modified simultaneously by means of the optical unit of the rotational device. The zoom or focus setting can be set manually, e.g. by means of operating wheels or sliders or the like, and/or in a motor-driven manner.

In general, an optical unit with a mirrored, in particular 180 degree-rotated image (e.g. 1:−1 image) requires a shorter installation length than an optical unit with a true-sided image (e.g. 1:1 image). In this respect, for reducing the installation length of the rotational device, an optical unit with a mirrored image offers advantages. Moreover, the number of lenses is smaller and the transmission quality is higher as a result. In order to display the image in a true-sided manner for the display at the screen, a corresponding conversion of the digital or analog image signals can be realized by means of additional hardware and/or software integrated in the evaluation unit 4b. Alternatively, the camera device 2 is connected with a 180-degree rotation to the proximal coupling means 610.

In order not to restrict the selection of usable evaluation units, it is alternatively possible to integrate an additional hardware component between a conventional evaluation unit 4b and the display device 5, said additional hardware component converting a mirrored image signal emanating from the evaluation unit 4b into a true-sided image and forwarding the latter to the display device 5. In one embodiment variant, this hardware component can also be combined in one unit with the control unit 4a in a mechanical and/or functional manner.

In the rotational devices depicted on the basis of FIGS. 1 to 9, the optical unit 63 is arranged in a bore 614 or in a channel or in a cavity at the stationary assembly 61. Alternatively, the optical unit can be arranged at the rotatable assembly in order to rotate with the latter. To this end, the rotatable assembly is, in particular deviating from the illustrations on the basis of FIGS. 3 to 9, at least partly arranged within the stationary assembly.

LIST OF REFERENCE SIGNS

1 Endoscope
10 Shaft
100 Distal end of the endoscope 1
101 Proximal end of the endoscope 1
11 Swivel prism at the distal end 100 of the endoscope 1
12 Eyepiece at the proximal end 101 of the endoscope 1
2 Camera device
20 Coupling means of the camera device 2
3 Holder for holding the rotational device 6
4a Control unit for controlling the rotational device 6
4b Evaluation unit for evaluating an image signal from the camera device 2 and for generating an image signal for the display device 5
5 Display device for displaying an image, controlled by the evaluation unit 4b
6 Rotational device for rotating the endoscope 2
60 Rotatable assembly of the rotational device 6
600 Distal coupling means at the rotatable assembly 60
601 Gearwheel at the rotatable assembly 60
602 Holding claw at the distal coupling means 600
603 Handwheel at the distal coupling means 600
603' Holding ring at the handwheel 603
604 Guide rail for pin 605 in the handwheel 603
605 Pin on the holding claw 602
606 Base part of the rotatable assembly 60
607 Opening at the rotatable assembly 60
608, 609 Bearing section of the rotatable assembly 60
61 Stationary assembly
610 Proximal coupling means at the stationary assembly 61
611 Opening at the proximal end of the stationary assembly 61
612 Holding ring at the stationary assembly 61
613 Shaft section of the stationary assembly 61
614 Bore (cavity) in the shaft section 613
62 Drive means for rotating the rotatable assembly 60 relative to the stationary assembly 61
620 Driveshaft of the drive means 62
621 Pinion at the driveshaft 620 of the drive means 62
622 Connecting piece for holding the drive means 62 at the stationary assembly 61
63 Optical unit in the bore 614 of the stationary assembly 61
630 Cover slip at the distal end of the optical unit 63 or of the bore 614
631, 632 Lens of the optical unit 63
633 Cover slip at the proximal end of the optical unit 63 or of the bore 614
634, 635 Achromat of the optical unit 63
64, 65 Bearing between the rotatable assembly 60 and the stationary assembly 61
66 Housing of the rotational device 6
660 Connector at the housing 66
661 Sealing ring between the housing 66 and the rotatable assembly 60
662, 663 Connection ports at the housing 66
67 Intermediate ring for restricting the rotation of the rotatable assembly 60 relative to the stationary assembly 61
670, 671 Stop at the intermediate ring 67
672 Stop at the rotatable assembly 60, corresponding to the stop 671 at the intermediate ring 67
673 Stop at the stationary assembly 61, corresponding to the stop 670 at the intermediate ring 67
α Viewing angle
L Longitudinal axis of the endoscope 1 and the optical axis of the optical unit 63 of the rotational device 6 and rotational axis of the rotatable assembly 60
O Light
P Patient
R Rotational motion about the longitudinal axis L
S Swivel axis of the swivel prism 11
V Swivel movement of the direction of view of the endoscope 1

The invention claimed is:

1. A rotational device for rotating an endoscope comprising
a stationary assembly;
a rotatable assembly rotatable relative to the stationary assembly;
a distal coupling at the rotatable assembly for coupling to an endoscope, the endoscope providing an optical image at or near the distal coupling;
a driver, which includes a motor that is embodied for putting the distal coupling into rotational motion in order to rotate an endoscope coupled to the distal coupling;
a proximal coupling at the stationary assembly for coupling to a camera device, the camera device registering the optical image and converting the optical image into an analog or digital signal;

an optical unit for transmitting the optical image from the distal coupling to the proximal coupling and for optically generating the optical image at or in the vicinity of the proximal coupling.

2. The rotational device according to claim 1, wherein the distal coupling is embodied for establishing a non-destructively detachable mechanical connection to an endoscope.

3. The rotational device according to claim 1, wherein the distal coupling is embodied for holding an eyepiece of the endoscope or a proximal end of the endoscope in a different way.

4. The rotational device according to claim 1, wherein the rotatable assembly is mounted at the stationary assembly in a manner rotatable about a longitudinal axis of an endoscope connected to the rotational device in an intended state.

5. The rotational device according to claim 4, wherein the optical unit is embodied for transmitting light from the distal coupling to the proximal coupling along the longitudinal axis.

6. The rotational device according to claim 4, wherein the optical unit comprises a first lens and a second lens offset along the longitudinal axis in relation to the first lens.

7. The rotational device according to claim 4, wherein the optical unit comprises a first achromat, a first lens, a second lens and a second achromat which are arranged in this sequence along the longitudinal axis, offset with respect to one another, in the optical beam path between the distal coupling and the proximal coupling.

8. The rotational device according to claim 1, wherein the optical image generated in a vicinity of the proximal coupling substantially corresponds to the optical image that is provided in a vicinity of the distal coupling by the endoscope with no change in image size.

9. The rotational device according to claim 1, wherein the optical unit is arranged in a cutout of a shaft section of the stationary assembly and the rotatable assembly is rotatably mounted about the shaft section.

10. The rotational device according to claim 1, wherein the proximal coupling is embodied as an eyepiece.

11. The rotational device according to claim 10, wherein the proximal coupling embodied as an eyepiece is embodied like an eyepiece of an endoscope to be connected to the distal coupling.

12. The rotational device according to claim 1, wherein the driver comprises a pinion which engages with a gearwheel of the rotatable assembly.

13. An endoscope device comprising:
a rotational device according to claim 1;
an endoscope for providing the optical image, the endoscope being connectable to the distal coupling of the rotational device;
a camera device for registering light from the endoscope and converting the light into an analog or digital signal, the camera device being connectable to the proximal coupling of the rotational device.

14. The endoscope device according to claim 13, wherein the endoscope comprises a shaft and a swivel prism, swivelable about a swivel axis and arranged at an end distant from the rotational device.

15. A method for rotating an endoscope, comprising the following steps:
coupling an endoscope to a distal coupling of a rotatable assembly, the endoscope providing an optical image at or near the distal coupling;
rotating the distal coupling with a motor-driven driver in order to put the endoscope connected to the distal coupling into rotational motion relative to a proximal coupling of a stationary assembly;
transmitting light from the distal coupling to the proximal coupling by an optical unit, the optical unit optically generating an image at or in the vicinity of the proximal coupling that substantially corresponds to the optical image provided at or near the distal coupling by the endoscope.

16. The method according to claim 15, furthermore comprising the following step:
coupling a camera device to the proximal coupling.

17. The rotational device according to claim 1, wherein the driver comprises an electric motor, an ultrasonic motor, or a piezo-motor.

18. The method according to claim 15, wherein the driver comprises an electric motor, an ultrasonic motor, or a piezo-motor.

19. An endoscope arrangement comprising:
an endoscope for providing an optical image; and
a rotational device having:
a stationary assembly;
a proximal coupling at the stationary assembly adapted to receive a camera for registering light from the endoscope and converting the light into an analog or digital signal;
a rotatable assembly rotatable relative to the stationary assembly;
a distal coupling at the rotatable assembly receiving the endoscope;
a motor adapted to rotate the distal coupling and the endoscope; and
an optical unit for transmitting light from the distal coupling to the proximal coupling, the optical unit optically generating an image at or in the vicinity of the proximal coupling that substantially corresponds to the optical image which is provided at or near the distal coupling by the endoscope.

20. The rotational device according to claim 1, wherein the optical unit comprises one or more lenses or other light-refracting elements.

* * * * *